United States Patent [19]

Taylor

[11] Patent Number: 4,789,397
[45] Date of Patent: Dec. 6, 1988

[54] METHODS OF INDUCING PLANT GROWTH RESPONSES

[75] Inventor: Fred R. Taylor, Wexford, Pa.

[73] Assignee: PPG Industries, Inc., Pittsburgh, Pa.

[21] Appl. No.: 7,552

[22] Filed: Jan. 28, 1987

[51] Int. Cl.$^4$ ............................................. A01N 37/10
[52] U.S. Cl. ..................................................... 71/107
[58] Field of Search ......................................... 71/107

[56] References Cited

U.S. PATENT DOCUMENTS 4,388,473  6/1983  Richter et al. ........................... 71/76

OTHER PUBLICATIONS

Watanabe et al., Chem. Abst., vol. 91, (1979) 69914x.
Eussen et al., Chem. Abst., vol. 95 (1981) 129416f.

*Primary Examiner*—Catherine L. Mills
*Attorney, Agent, or Firm*—Alice C. Brennan

[57] ABSTRACT

Desirable growth responses, such as, for example, a retardation of abscission layer formation, or an increase in the size, yield quality or sugar content of fruit are induced in fruit bearing plants by applying to the fruit or to the plant prior to harvest an effective amount of substituted benzoic or phenylacetic acid ester.

10 Claims, No Drawings

METHODS OF INDUCING PLANT GROWTH RESPONSES

FIELD OF THE INVENTION

Desirable growth responses, such as, for example, a retardation of abscission layer formation, or an increase in the size, yield, quality or sugar content of fruit are induced in fruit bearing plants by applying to the fruit or to the plant prior to harvest an effective amount of substituted benzoic or phenylacetic acid ester.

THE INVENTION

Commonly assigned U.S. Pat. No. 4,388,473 discloses substituted benzoic acids or phenylacetic acetic acids and esters thereof which when applied to the locus of a plant, inhibit meristematic activity, resulting in inhibition of plant growth. It has now surprisingly been found that certain of the compounds described in U.S. Pat. No. 4,388,473 induce other desirable plant growth responses, which include the following:

1. Retard abscission layer formation in pome fruits, e.g., apples or pears, which decreases pre-harvest fruit drop resulting in increased useable fruit yield.
2. Increase bloom set in nuts, e.g., almonds, walnuts, pecans or pistachio nuts, resulting in increased nut set and nut yield.
3. Increase the size, quantity and yield of e.g., peaches, apricots or cherries; as well as reduce pre-harvest drop, i.e., "June drop" of peaches.
4. Increase the size and quality of tubers, e.g., potatoes and yams.
5. Increase the sugar content (Brix) and accelerate ripening of grapes.

The foregoing growth responses are induced in accordance with this invention by applying to the plant or locus thereof an effective growth response inducing amount of a compound of the Formula I:

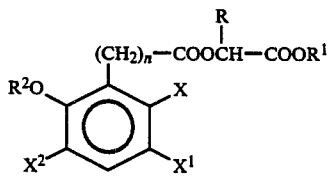

wherein
X, $X^1$ and $X^2$ are hydrogen or halogen provided that X and $X^2$ or $X^1$ and $X^2$ must be halogen;
R is hydrogen or $C_1$ to $C_6$ alkyl;
$R^1$ is hydrogen or $C_1$ to $C_{10}$ alkyl, haloalkyl or alkoxyalkyl, alkali metal or ammonium;
n is 0 or 1; and
$R^2$ is $C_1$ to $C_4$ alkyl.

Preferred compounds of the Formula I are those wherein X and $X^2$ are halogen and $X^1$ is hydrogen, $X^1$ and $X^2$ are halogen and X is hydrogen, n is 0, R is hydrogen or methyl, $R^1$ is hydrogen or $C_1$ to $C_4$ alkyl and $R^2$ is $C_1$ or $C_2$ alkyl. Most preferred compounds of the Formula I are those wherein X and $X^2$ are chlorine and $X^1$ is hydrogen, $X^1$ and $X^2$ are chlorine and X is hydrogen, n is O, R is methyl, $R^1$ is hydrogen or ethyl and $R^2$ is methyl.

The compounds of Formula I are fully described in commonly assigned U.S. Pat. No. 4,388,473, the teachings of which are incorporated by reference herein as though fully set forth.

The following Examples are illustrative of the use of certain of the Formula I compounds for inducing various growth responses in accordance with this invention. All of the results and observations described in the following Examples were determined and made under actual field conditions at various locations within the continental United States. The Formula I compounds which were used in the tests are as follows A. The compound, 2,5-dichloro-6-methoxy benzoic acid, (ethoxycarbonyl)ethyl ester, represented by the following formula:

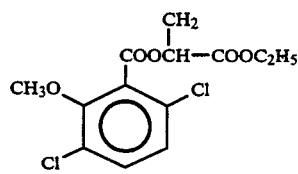

B. The compound, 3,5-dichloro-6-methoxy benzoic acid, (ethoxycarbonyl)ethyl ester, represented by the following formula:

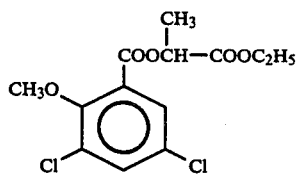

C. The compound, 2,5-dichloro-6-methoxy benzoic acid, lactate ester represented by the formula:

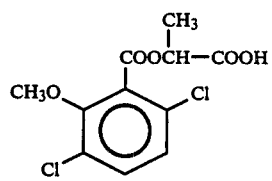

EXAMPLE 1

This Example illustrates the effect of the method of this invention in retarding abscission layer formation in apples as measured by the increase in pull force required to remove apples from the trees, fruit drop and flesh firmness.

Aqueous solutions containing various parts per million (ppm) concentrations of each of the above described compounds A, B and C were prepared and foliar sprayed with a hand gun at a rate of 400 gallons per acre on Golden Delicious apple trees one week prior to harvest. The spray was applied just to the point of run-off or drip and single tree treatments were replicated six times. Seven days after treatment the pull force required to remove apples from the trees was measured using a Chatillon pull-push force gauge. Fifteen apples per replicate tree were sampled totalling ninety apples per treatment. The following table gives the mean pull force in pounds for each treatment as compared with an untreated control.

| Treatment | Pull Force |
| --- | --- |
| Control | 5.9 |
| A @ 25 ppm | 6.4 |
| A @ 100 ppm | 5.6 |
| A @ 200 ppm | 6.9 |
| B @ 25 ppm | 6.8 |
| B @ 50 ppm | 7.3 |
| B @ 100 ppm | 6.8 |
| C @ 25 ppm | 6.7 |
| C @ 50 ppm | 6.2 |
| C @ 100 ppm | 6.6 |

Analyses of the raw date summarized in the foregoing table indicates statistically greater pull force for compound A at a 200 ppm concentration, compound C at a 25 ppm concentration, and compound B at all three concentrations versus the untreated control, at a 95 percent level of confidence.

Red delicious apple trees were treated in like manner, i.e., by spraying, at a rate of 400 gallons per minute, aqueous solutions of various parts per million concentrations of compounds A, B and C one week prior to harvest. Each single tree treatment was replicated four times. Seven days after treatment the fruit that had naturally dropped from each tree were counted and recorded. Also, seven days after treatment the flesh firmness of the undropped fruit was measured using a McCormick, pressure tester. Twenty-five apples per replicate tree were sampled for a total of one hundred apples per treatment. The following table gives the mean quantity of dropped fruit and the mean flesh measured in pounds per square inch for each treatment as compared with an untreated control.

| Treatment | Fruit Drop | Firmness |
| --- | --- | --- |
| Control | 56.25 | 8.17 |
| A @ 25 ppm | 38.50 | 9.12 |
| A @ 100 ppm | 46.00 | 10.07 |
| A @ 200 ppm | 77.00 | 10.87 |
| B @ 25 ppm | 59.75 | 9.85 |
| B @ 100 ppm | 46.75 | 11.20 |
| B @ 200 ppm | 20.50 | 9.07 |
| C @ 25 ppm | 19.75 | 9.37 |
| C @ 50 ppm | 27.00 | 10:27 |
| C @ 100 ppm | 18.25 | 8.67 |

Analyses of the raw data summarized in the foregoing table indicates that treatments with compound C at all concentrations and compound B at 100 ppm concentration result in statistically less fruit drop than the untreated control whereas all of the treatments at all of the tested concentrations resulted in statistically increased ripening resistance at a 95 percent level of confidence.

EXAMPLE II

This Example illustrates the effect of the method of this invention in increasingly bloom set, nut set and nut yield in almond crop.

Several field trials at various sites were conducted to determine the growth response effect of compound A on almonds. In all of the trials aqueous solutions containing compound A in concentrations ranging from 12 to 50 ppm were applied by foliar spray to mature almond trees at various stages of bloom. The rate of application was 400 gallons per acre and application was made just to the point of run-off or drip. Application timing ranged from the pink bud stage to the 100 percent bloom stage. Nut set data was taken after "June drop" by monitoring the number of nuts set per 100 blossoms per replication. The data indicated that compound A had a positive effect on nut set, the nut set at one test site ranging from 75 to 99 percent compared to an untreated control nut set of 61 percent. In one of the field trials a severe frost occurred at the bloom stage which, of course, resulted in decreased nut set. However, basis the control, treatment in accordance with the invention appeared to provide a degree of frost protection. Bases the results of these field tests, the data strongly suggests that compound A, when applied to almonds during early bloom, will increase bloom set with a concomitant increase in nut set and nut yield. It appears that optimum timing of application would be at the popcorn or pre-bloom stage at a concentration of about 25 to 50 ppm of active compound.

EXAMPLE III

This Example illustrates the growth response induced by the method of this invention on freestone peach varietals.

A number of field trials at various sites were conducted to determine the growth response effect of compound A on peaches. In all of the trials dilute aqueous solutions containing compound A in concentrations ranging from 12 to 200 parts per million were applied by foliar spray to the point of run-off or drip to mature peach trees. Application timing ranged from pre-bloom through 100 percent bloom. In general, positive plant growth responses were observed, namely increases in leaf area, green coloration and total photosynthesis. Also, treatment according to the method of this invention generally increased fruit yield per tree. Although the increased yield response generally was the result of increased fruit size, in one trial the increased yield was due primarily to the ability of the trees to grow additional fruit. Also observed were trends toward positive color enhancement of the fruit, increased firmness and an increase in soluble solids which appear to enhance maturity.

In summary, analyses of the data and information amassed from the various field trials indicate that in most instances treatment of freestone peach trees in accordance with the method of this invention tends to increase the growth of the trees, resulting in an increase in leaf area, fruit size and ability of the tree to bear more fruit. Also, appearance, soluble solids and firmness of the fruit appear to be favorably enhanced. Also, bases these field trials, the most consistent results appear to obtain when the peach trees are treated early in the bloom cycle, i.e., between the red bud and first bloom stages using solutions containing from about 25 to about 100 ppm of formula I compound.

EXAMPLE IV

This Example illustrates the effect of the method of this invention on increasing quality and yield of potato crop.

Several trials were conducted under actual field conditions to determine the growth response effect on potatoes of the method of this invention.

Aqueous solutions containing various parts per million concentrations of compound A were applied by spraying, to potato plants at various stages of growth. In general, it was observed that treatment in accordance with the invention resulted in a tendency to produce a higher proportion of larger, i.e., greater than or equal to 10 ounces, potatoes. For example, at one test site, aqueous solutions containing 75, 100 and 125 parts per million of compound A were applied to Russet Burbank potatoes at the pre-tuber initiation (PTI) or stolon hooking stage, and at 7 to 10 days after tuber initiation or the post-tuber initiation (POTI) stage. At harvest yield increases of from 1.5 to 7.0 tons per acre resulted at the pre-tuber initiation (PTI) application timing and yield increases of from 1 to 5.5 tons per acre resulted at the post-tuber initiation (POTI) timing, the lower application rates giving the higher yields at both application timings. Also, the PTI and POTI applications also increased the percentage of tubers greater than or equal to 10 ounces weight by from 8 percent to almost 14 percent as compared with the untreated control. The results of this trial are summarized in the following table.

| Treatment | Useable Yield Tons/Acre | % Tubers ≧ 10 oz. |
|---|---|---|
| Control | 24.0 | 24.5 |
| PTI @ 75 ppm | 31.0 | 37.9 |
| PTI @ 100 ppm | 27.3 | 33.5 |
| PTI @ 125 ppm | 25.4 | 38.0 |
| POTI @ 75 ppm | 29.4 | 32.6 |
| POTI @ 100 ppm | 28.8 | 35.4 |
| POTI @ 125 ppm | 25.0 | 38.4 |

Specific gravities of the treated and control potatoes did not differ significantly. Although there was a trend toward increased hollow heart and brown center in the treated potatoes, there was also an increase in apical glucose content. Also, fry color analysis on treated potatoes held in long term storage resulted in treated potatoes having more desirable fry color than untreated potatoes.

EXAMPLE V

This Example illustrates the effect of the method of this invention on accelerating ripening of grapes as indicated by increased sugar content.

Several field trials were conducted to determine the growth response effect of compound A on grapes, particularly on Thompson and Flame seedless table varieties. In all of the trials aqueous solutions containing compound A at concentrations ranging from 25 to 100 parts per million (ppm) were applied at a rate of 200 gallons per acre at various stages of growth ranging from pre-bloom to post-bloom. The treatments in accordance with the invention were made in conjunction with conventional treatments with gibberellic acid, which is commonly used in the grape growing industry for cluster elongation and to increase berry size. In all of the trials, regardless of application timing or concentration of the treatment solution, a positive increase in grape sugar content (Brix) was observed, as well as an increase in Brix/acid ratio. Also, in one trial a reduction in the degradation of the rachis of the grape bunch, as measured by the extent of bunch shatter, was observed. The data and information gathered from these field trials indicate that Formula I compound when applied to grapes in concentrations of from 50 to 100 ppm will provide an increase in Brix to an extent which could enable harvest of the grape crop as much as two weeks prior to normal harvest, which affords a grower a two-fold advantage. Firstly, since timing of harvest is dictated by marketing orders which set the minimums for Brix and Brix/acid ratio, a grower could market the grape crop earlier than normal and thus command a premium price. Secondly, the early ripening would be desirable in late ripening varieties where rain or cool weather would retard the ripening process.

The foregoing Examples illustrate the growth responses induced by the methods of this invention on 2 variety of fruiting bodies. It is not intended that the methods of the invention be limited to those fruiting bodies specifically exemplified, since it is believed that similar desirable growth responses can be induced in a wide variety of fruiting bodies, which can readily be empirically determined by those skilled in the art. Of course, the growth response inducing compounds of formula I can be used as such or in formulation with other agronomically acceptable adjuvants or additives. The formula I compounds, whether or not formulated with other agronomically acceptable materials, may be applied in the form of dusts, granules, wettable powders, solutions, suspensions, aresols, emulsions, dispersions or the like in a manner well know to the art.

I claim:

1. A method of inducing growth response, other than inhibition of meristematic activity, in fruit bearing plants by applying to the fruit or to the plant prior to harvest a growth response inducing amount of a compound of the formula:

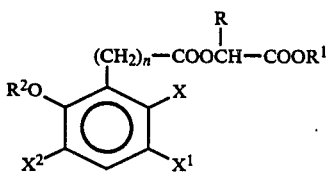

wherein
X, $X^1$ and $X^2$ are hydrogen or halogen provided that X and $X^2$ or $X^1$ and $X^2$ must be halogen;
R is hydrogen or $C_1$ to $C_6$ alkyl;
$R^1$ is hydrogen or $C_1$ to $C_{10}$ alkyl, haloalkyl or alkoxyalkyl, alkali metal or ammonium;
n is 0 or 1; and
$R^2$ is $C_1$ to $C_4$ alkyl.

2. The method of claim 1 wherein the growth responsing inducing compound is one wherein X and $X^2$ are halogen, $X^1$ is hydrogen, n is O, R is hydrogen or methyl, $R^1$ is hydrogen or $C_1$ to $C_4$ alkyl and $R^2$ is methyl or ethyl.

3. The method of claim 2 wherein the growth response inducing compound is one wherein X and $X^2$ are chlorine, R is methyl, $R^1$ is hydrogen or ethyl and $R^2$ is methyl.

4. The method of claim 1 wherein the growth wherein $X^1$ and $X^2$ are halogen, X is hydrogen, n is 0, $R^1$ is hydrogen or methyl, R is hydrogen or $C_1$ to $C_4$ alkyl and $R^2$ is methyl or ethyl.

5. The method of claim 4 wherein the growth response inducing compound is one wherein $X^1$ and $X^2$ are chlorine, R is methyl, $R^1$ is hydrogen or ethyl and $R^2$ is methyl.

6. The method of claim 1 wherein the fruit is selected from apples or pears and the growth response is manifested by a retardation of fruit abscission.

7. The method of claim 1 wherein the fruit is selected from almonds, walnuts, pecans or pistachio nuts and the growth response is manifested by an increase in blossom set.

8. The method of claim 1 wherein the fruit is selected from peaches, apricots or cherries and the growth response is manifested by an increase in size or quantity.

9. The method of claim 1 wherein the fruit is potatoes and the growth response is manifested by an increase in size.

10. The method of claim 1 wherein the fruit is grapes and the growth response is manifested by an increase in sugar content.

* * * * *